United States Patent [19]

Knutson et al.

[11] Patent Number: 5,416,582
[45] Date of Patent: May 16, 1995

[54] METHOD AND APPARATUS FOR LOCALIZATION AND SPECTROSCOPY OF OBJECTS USING OPTICAL FREQUENCY MODULATION OF DIFFUSION WAVES

[75] Inventors: Jay R. Knutson, Kensington; Alexander Knuttel; Joseph M. Schmitt, both of Rockville, all of Md.

[73] Assignee: The United States of America as represented by the Department of Health and Human Services, Washington, D.C.

[21] Appl. No.: 15,983
[22] Filed: Feb. 11, 1993
[51] Int. Cl.⁶ .................... G01B 9/02; A61B 5/05
[52] U.S. Cl. .................... 356/349; 128/633; 128/665; 128/653.1; 356/345
[58] Field of Search ........... 356/349, 345; 128/633, 128/665, 653.1

[56] References Cited

U.S. PATENT DOCUMENTS

| | | | |
|---|---|---|---|
| Re. 33,643 | 7/1991 | Isaacson et al. | 128/633 |
| 3,273,458 | 9/1966 | Kohler | 88/61 |
| 3,400,363 | 9/1968 | Silverman | 340/3 |
| 3,670,098 | 6/1972 | Korpel | 178/6 |
| 3,748,470 | 7/1973 | Barrett | 250/363 |
| 3,802,759 | 4/1974 | Andersson | 350/7 |
| 3,831,031 | 8/1974 | Barrett et al. | 250/363 |
| 3,860,821 | 1/1975 | Barrett | 250/363 |
| 3,939,348 | 2/1976 | Barrett | 250/339 |
| 3,961,191 | 6/1976 | Stoner et al. | 250/312 |
| 4,118,106 | 10/1978 | Leith | 350/96.25 |
| 4,146,295 | 3/1979 | Fonrojet et al. | 350/3.66 |
| 4,165,462 | 8/1979 | Macovski et al. | 250/363 |
| 4,277,127 | 7/1981 | Smith et al. | 350/3.67 |
| 4,407,290 | 10/1983 | Wilber | 128/633 |
| 4,435,838 | 3/1984 | Gourlay | 382/68 |
| 4,442,455 | 4/1984 | Huignard et al. | 358/209 |
| 4,446,871 | 5/1984 | Imura | 128/633 |
| 4,467,812 | 8/1984 | Stoller | 128/644 |
| 4,515,165 | 5/1985 | Carroll | 128/644 |
| 4,600,308 | 7/1986 | Waite | 356/363 |
| 4,649,275 | 3/1987 | Nelson et al. | 250/358.1 |
| 4,651,743 | 3/1987 | Stoller | 128/664 |
| 4,767,928 | 8/1988 | Nelson et al. | 250/341 |
| 4,773,422 | 9/1988 | Isaacson et al. | 128/633 |
| 4,786,124 | 11/1988 | Stone et al. | 350/3.7 |
| 4,805,627 | 2/1989 | Klingenbeck et al. | 128/653 |
| 4,860,253 | 8/1989 | Owechko et al. | 365/125 |
| 4,910,404 | 3/1990 | Cho et al. | 250/358.1 |
| 4,922,919 | 5/1990 | Novack | 128/633 |
| 4,945,239 | 7/1990 | Wist et al. | 250/358.1 |
| 4,948,974 | 8/1990 | Nelson et al. | 250/358.1 |
| 4,998,018 | 3/1991 | Kurahashi et al. | 250/343 |
| 5,022,757 | 6/1991 | Modell | 356/318 |
| 5,090,415 | 2/1992 | Yamashita et al. | 128/665 |
| 5,137,355 | 8/1992 | Barbour et al. | 356/342 |
| 5,203,339 | 4/1993 | Knüttel et al. | 128/665 |
| 5,213,105 | 5/1993 | Gratton et al. | 128/665 |

FOREIGN PATENT DOCUMENTS

| | | | |
|---|---|---|---|
| 0458601 | 11/1991 | European Pat. Off. | 356/349 |
| WO9009003 | 8/1990 | WIPO | 356/349 |
| WO9300045 | 1/1993 | WIPO | 356/349 |
| WO9309423 | 5/1993 | WIPO | 356/349 |

OTHER PUBLICATIONS

Knuttel, *Improvement of Spatial Resolution in Reflectance Near–Infrared Imaging by Laser–Beam Interference*, SPIE, vol. 1640, Jan. 1992.

Feddersen et al., *Digital Parallel Acquistion in Frequency Domain Fluorometry*, 60 Rev. Sci. Instrum. 2929, 1989.

J. Fiskin et al., *Diffusion of Intensity Modulated Near–Infrared Light in Turbid Media*, Proc. SPIE, 1431, 122–135, 1991.

Gratton et al., *A Continuously Variable Frequency Cross–Correlation Phase Fluorometer With Picosecond Resolution*, Biophysical Journal, vol. 44, 315–325, 1983.

*Primary Examiner*—Rolf Hille
*Assistant Examiner*—Minhloan Tran
*Attorney, Agent, or Firm*—Foley & Lardner

[57] ABSTRACT

An apparatus and method for using frequency modulated diffusive photon-density waves propagating through a turbid medium such as tissue for detecting optical properties of objects and for imaging objects within the turbid medium. Frequency modulation enables real time differential measurement of the interaction of different colors with the object when the different colors are chosen such that they react the same with the medium but differently with the object. The method greatly simplifies optical imaging and increases the amount of information which may be obtained about the object.

21 Claims, 7 Drawing Sheets

METHOD AND APPARATUS FOR LOCALIZATION AND SPECTROSCOPY OF OBJECTS USING OPTICAL FREQUENCY MODULATION OF DIFFUSION WAVES

BACKGROUND OF THE INVENTION

Numerous techniques and devices are known and available for imaging structures or objects within opaque or turbid mediums, such as biological tissues. Various examples and a description of such techniques are described in related applications, Ser. No. 07/722,823 (filed Jun. 29, 1992), entitled "Method and Apparatus for Imaging a Physical Parameter in Turbid Media Using Diffusive Waves," and Ser. No. 07/789,517 (filed Nov. 8, 1991), entitled "Multidimensional Imaging Using a Single Point Detector for a Phase Encoded Modulated Optical Carrier," the respective contents of which are incorporated herein by reference. Various principles embodied in such techniques are further set forth in Knuttel et al., *Improvement of Spatial Resolution in Reflectance Near-Infrared Imaging by Laser-Beam Interference*, SPIE—The International Society of Optical Enginerring: Time-Resolved Laser Spectroscopy in Biochemistry III, vol. 1640 (January 1992), Feddersen et at., *Digital Parallel Acquisition in Frequency Domain Fluorometry*, 60 Rev. Sci. Instrum. 2929 (1989) (heterodyne down beating to process signals from diffuse photon density waves), and J. Fiskin et al., *Diffusion of Intensity Modulated Near-Infrared Light in Turbid Media*, Proc. SPIE, Time-Resolved Spectroscopy and Imaging of Tissues, 1431, 122–135 (1991) (describing the properties and mathematic models for diffuse photon density waves propagating through turbid medium), the respective contents of each of which also are incorporated herein by reference.

The previous methods for spatial localization and imaging through highly scattering media have extended near-infrared spectroscopy by introducing time-resolved techniques. One objective of such imaging is to spatially localize or image optical parameters, like absorption, which is often times different in healthy and cancerous or ischemic tissues. A discussion of these prior techniques and their underlying principles is set forth below.

A diffuse photon density wave is produced when photons from a source of light penetrate a turbid media with a thicknesses exceeding about 10 times the mean-free path of the photon and are multiply scattered therein. The photons propagating through the medium in the diffuse photon density wave are scattered and absorbed such that any coherence in the individual wavelengths of the photons is lost. However, the photon density wave (i.e., a wave propagating through the medium representing the density of the photons) moves through the medium with a coherent wave front. Previous techniques have attempted to obtain information about the medium and objects located in the medium by exploiting the information contained in the diffuse photon density waves, since the propagation depends on the properties of the medium. Various techniques have been proposed both in reflectance-mode and transmittance-mode for optically imaging (i.e., examining optical properties) in biological tissues thicker than a few millimeters. The photon density wave, particularly in reflectance-mode imaging, contributes overwhelmingly to the detected signal because the number of re-emitted (quasi-) ballistic photons (i.e., photons not scattered or absorbed) is extremely low.

Prior art techniques, such as those described in the above-mentioned related applications and publications, have increased the amount of information obtainable from the diffuse wave by the use of intensity (i.e., amplitude) modulation and phase modulation of the source of imaging electromagnetic radiation (e.g., a laser beam). In diffusive wave optics, the wavelength and attenuation of an intensity-modulated photon-density wave are complex functions of modulation-frequency and absorption. Nonetheless, at a given modulation frequency, the photon-density wave travels with constant phase velocity in a homogeneous tissue, which implies that its phase-front maintains coherence. The wavelength of a diffusive photon density wave increases as the absorption increases, because long photon paths become less likely. Attenuation of the diffusive photon density wave is exponential as it propagates through a turbid medium.

Two types of detection systems are used for optical imaging. The term "reflectance mode" refers to the situation where the detector is located on the same side of the medium as the source of light and detects light returning from the medium. The term "transmission mode" detection is used when the detector is placed on the opposite side of the medium detecting light traveling through the medium. The reflectance mode has, compared to the transmission mode, the advantage that very thick (in vivo) objects can be probed, as long as the region of interest is not greater than a few centimeters deep. In some conventional source/detector arrangement, photons returning from regions close to the surface tend to overwhelm those returning from deeper regions. Therefore, the acquired signal is most sensitive to absorbing bodies or emitting probes in the medium located in superficial regions close to the source or the detector.

One objective of more recent prior art imaging devices is to eliminate the problems associated with photons returning from near the surface which tend to overwhelm the detector. In order to enhance spatial localization (imaging) of absorbing or fluorescent bodies deep inside a turbid medium, interfering photon density waves have been produced by various dual laser-source configurations and detected by a single detector or a gated, intensified CCD (ICCD) camera. Utilizing these techniques, two problems associated with traditional reflectance-mode imaging have been ameliorated: (a) the dominance of surface signals and (b) the poor sensitivity to changes in the position of an absorbing body located deep within the medium.

In order to better understand the instant invention an illustration of such a prior art imaging technique is provided. FIG. 1 shows a frequency-domain spectrometer according a prior technique which is configured to image an object embedded in tissue with two interfering diffusive photon density waves and to detect the magnitude and phase of the re-emitted light. In FIG. 1, the spectrometer has a detector 60. The detector is based on either the photo-multiplier tube (PMT) 61a or a gated, intensified CCD (ICCD) camera 61b. A cw mode-locked Nd:YAG laser 101 (Spectra Physics, Model 3400) pumps a cavity dumped dye laser 102 (Model 3510/3295) to produce pulses of ~10 ps duration at a repetition rate of 4.1 MHz. The average power is about 100 Mw at an optical wavelength of 605 nm and 150 Mw at 575 nm. A small portion of the beam is directed onto a photodiode or onto a few outer pixels of the ICCD camera via mirrors M₁, M₂, beam-splitter Bs₁, and mirrors M₃, and M₄ to provide a reference signal. Another beam-splitter BS₂ divides the main part of the intensity-modulated beam into two beams 400 and 500. When the device is operated in an asymmetrical mode, beam 400 and beam 500a are applied to the same side of the turbid medium 20 as compared to the detector 60. In the symmetrical configuration, beam 400 and beam 500b are centered around the detector. The two types of configurations are accomplished by inserting and removing mirror M1b. The path length (and therefor phase) of beam 500 can be adjusted by a prism 103 mounted on a rail. The intensity ratio of the two beams is varied by attenuating beam 400 with a variable neutral-density filter 104. The beams 400 and 500a or 500b are directed to a turbid medium 20 having an object 30 therein. The light exiting the object is focused via a relay lens 62 through aperture A and onto detector 60. When using the detector 61a, the PMT signal, as well as the PD signal, are mixed down externally by super-heterodyning via an intermediate frequency of 200 kHz. The filtered audio-frequency signal (40 Hz) is acquired with an A/D converter (Keithley). When using the detector including ICCD 61b, a high-frequency sine wave is applied to the intensifier of the ICCD, operating in a fairly linear part of its characteristic curve, to mix the signals internally; the resulting 1 Hz signal is acquired by a frame grabber (Data Translation). The neutral-density filter 105 adapts the light-intensity range to the dynamic range of the particular detection system.

The apparatus of FIG. 1 enables two types of imaging to be preformed, both with the aid of two interfering photon density waves. The apparatus may be used to detect an absorbing body deep inside the turbid medium 20 by desensitizing the region close to the surface. This is accomplished using the asymmetric laser-beam 400 and 500a configuration and the single-detector 61a arrangement. The second type of imaging spatially localizes (images) fluorescent objects inside the medium (20). This is accomplished with the symmetrical laser beam 400 and 500b configuration. The excitation of a fluorescent object may be determined by the phase and magnitude of the photon density at a given location which defined the destructive interference pattern. Light at an excitation wavelength (e.g., 575 nm) is blocked by an optical filter 63 so that transmitted light within a narrow band of wavelength (e.g., 610 nm) around the known emission peak of the fluorescent object is provided to the ICCD camera detection configuration 61b.

For both types of imaging, destructive interference at a given point in the medium is accomplished by adjusting the magnitude and phase of both laser beams until the AC magnitude at that point becomes vanishingly small. This null condition indicates that the AC magnitudes of the diffusing photon density waves produced by the two incident sources are equal in magnitude and 180° out of phase at this point. Imaging data may also be collected utilizing the characteristic of constructive interference. This is accomplished by shifting the phase of beam 500 via prism 103 by 180°.

Imaging may be performed by the described apparatus in accordance with the following principles. A prediction of the effect of the position of an absorbing body on the phase and magnitude of the detected signal at a particular frequency can be mathematically approximated. For detecting absorption, the asymmetric laser-beam illumination beam 400 and 500a and signal-point detection apparatus 61a is used. Similarly, a prediction of the illumination pattern in a turbid medium produced by symmetrically positioned laser beams can be calculated using an analytical expression. An object 30 inside the turbid medium 20 is imaged by reference to predicted properties of the diffuse photon density wave in a homogeneous turbid medium. The detected results are interpreted in accordance with the expected characteristics of the diffuse waves in such a turbid medium.

While several mathematical models, including Gaussian-convolution, Monte-Carlo, finite-element, and finite-difference methods, are applicable to all kinds of body/background geometries characterized by a wide range of scattering and absorption coefficients, the principal of time-dependent diffusion of photons as detected by the above apparatus is sufficiently understood using the finite-difference method.

The diffuse photon density $\Phi(r,t)$ at a given point r and time t can be determined using the time-dependent diffusion equation, $$\frac{1}{c_n} \frac{\partial}{\partial t} \Phi(r,t) - D\nabla^2 \Phi(r,t) + (\mu_{ab} + \mu_a(r))\Phi(r,t) = S(r,t) \quad (1)$$

where $S(r,t)$ represents the intensity of the photon source. The speed of light in the medium is $c_n = c/n$, where n is the refractive index of the medium and c is the vacuum light speed. The term $\mu_{ab} + \mu_a(r)$ is the total absorption coefficient which is given by the sum of the background absorption coefficient, $\mu_{ab}$, and a space-dependent absorption coefficient representing that of the absorbing body, $\mu_a(r)$. The diffusion coefficient is defined in terms of $\mu_{ab}$ and transport-corrected scattering coefficient, $\mu_s'$, as $$D = \frac{1}{3(\mu_{ab} + \mu_s')} \quad (2)$$

In a turbid medium of anisotropic scatterers, $\mu_s'$ can be much less than the isotropic scattering coefficient $\mu_s$. The anisotropy parameters of most biological tissues are between 0.8 and 0.97, yielding values of $\mu_s'$ typically a factor of 5 to 30 times less than $\mu_s$.

In accordance with the above calculations, and in particular the diffuse equation (1), the data obtained using the above apparatus can be interpreted. A more detailed explanation of the calculations and characteristics of an intensity modulated diffuse photon density wave propagation is provided in Fiskin et al. mentioned above. FIGS. 2a)-2d) show plots of the intensity and phase data which are produced when an absorbing body is positioned at various locations in the depth and lateral directions. Such imaging is performed using the asymmetric illumination conditions and a single detector (PMT) depicted in FIG. 1. By way of example, these graphs illustrate imaging using a modulation-frequency of 410 MHz where the absorption coefficient, $\mu_{a1}$, of the object to be detected is 17.5 times higher than the background absorption under simulated conditions. The spatial zero point for this plot is referenced to the spot where the light exits the medium 20 through the detector 60 aperture. Magnitudes, when using either destructive and constructive interference are normalized to the maximum signal recorded under constructive interference conditions.

As can be seen in FIGS. 2a)-2d), when using this apparatus, the sensitivity is reduced close to the surface.

This is because destructive interference occurs in this region. With increasing depth of the absorbing body, the AC magnitude reaches a maximum and finally drops again. Therefore, the region of greatest sensitivity to the absorbing body is crudely localized. The most sensitive region (maximum AC magnitude) under the above conditions is about 13 mm deep for lateral positions close to the detector. The sensitivity maximum shifts closer to the surface as the location of the absorber shifts to positions near the entry point of beam 500$a$ in FIG. 1. In FIG. 2$b$), a large phase change vs. depth is apparent. Contrast this with the data obtained under constructive-interference conditions shown in FIGS. 2$c$) and 2$d$). The magnitude decrease is plotted relative to the maximum signal at the deepest body location to allow comparison with the destructive case. As seen in FIG. 2$d$), the phase gradient measured under constructive-interference conditions is much smaller than that measured under destructive-interference conditions.

It can further be realized that as the absorption coefficient of an object to be detected changes, the AC magnitude and the phase signals of the detected body vary as shown in FIG. 3. FIGS. 3$a$ and 3$b$ show the relationship between the absorption coefficient and the AC magnitude and phase signals, respectively. The magnitude and phase results are plotted vs. object position in the depth dimension for an object which is laterally displace 20 mm from the detector (located between beam 400 and detector 60 aperture). The magnitude plots have similar shapes, but the change induced by the low absorption body is substantially less than that induced by the high absorption body. While magnitude signals are sensitive to the absorption coefficient of the body, the phase signal is relatively invariant with respect to this parameter.

According to the above apparatus, destructive and constructive interference of diffusive photon density waves may be used to accomplishes two useful functions central to the problem of locating absorbing bodies and imaging fluorescent objects in a turbid medium. First, with respect to the localization of an absorbing body, the region of maximum sensitivity can be shifted deeper into the medium using an asymmetrical laser-beam arrangement. This allows an immediate crude localization. Second, spatially selective excitation of a fluorescent probe in a scattering volume can be achieved by adjusting the phases and magnitudes of two laser beams incident on the surface to establish destructive interference in desired regions. The use of an ICCD camera facilities the simultaneous acquisition of the phase and magnitude signals needed to reconstruct high-resolution images.

Other ways of employing diffusive-wave interference for localization/imaging have been suggested. In FIG. 4, for example, the shapes of the null regions for two different incident beam-intensity ratios and phase differences are depicted which could be directly exploited to localize fluorescent probes in two dimensions. Such contour plots can be calculated using the diffuse wave calculations described above. The magnitude ratios plotted in FIGS. 4$a$) and 4$c$) demonstrate that constructive and destructive interference patterns differ significantly only in the vicinity of the null point. It has been considered that by combining the calculated destructive/constructive ratios (FIGS. 4$b$) and 4$d$)) obtained for different source positions, a well-defined region of localization can be established, as illustrated in FIG. 4$e$). Since the signal in the null region is almost zero (noise floor) the position of the peak indicates the region of complete destructive interference very well. While these imaging predictions show the potential for developing multiple-beam systems in imaging applications, modeled after "beam steering" techniques employed in phased-array radar, it is extremely cumbersome to calculate the interference patterns and exploit these possibilities. An even more challenging task of imaging embedded absorbers is believed possible by the above technique by ratioing phase and magnitude signals obtained under different interference conditions to reduce the effects of shallow-penetrating photons that do not interact with the absorbers. Such techniques are still complicated due to the extreme complexity that is associated with the propagation (due to scattering and absorption by the medium) of the photon density waves.

A common problem associated with each of the above techniques is that they involve interpreting complicated diffuse wave interference patterns and output, making it extremely difficult to isolate the portions of the actual output which are due only to the object in question (i.e., filter out the portions of the output which is not due to the object to be imaged and therefore does not contain any useful information). Further, since the useful information is carried in the same domain as the unwanted information the equipment must have extreme precision in order to maintain an acceptable signal to noise ratio. As a result of these problems, use of such apparatus for imaging purposes has been substantially limited.

SUMMARY OF THE INVENTION

The object of the instant invention is to provide an optical imaging technique for imaging an object within a turbid medium which is free from the above described disadvantages. More particularly, an object of the invention is to provide an apparatus and method for determining optical properties (e.g., imaging objects or detecting discolorations) within turbid tissue capable of providing increased detail about the object while simplifying the process of screening out unwanted characteristics of diffuse waves coming from the medium. A further object of the instant invention is to carry the useful data in a new and different domain (i.e., color due to frequency modulation) not directly connected to the unwanted information in the complex output. Such an imaging device may be used, for example, to pre-screen and image discolorations in cancerous tissue at an earlier stage than possible by conventional transmission (e.g., x-ray) devices.

The instant invention can be applied independent of or in conjunction with the above mentioned techniques (e.g., using constructive and destructive interference) thereby increasing the obtainable information.

Accordingly, the instant invention incorporates the novel use of frequency modulation in conjunction with the amplitude modulated source of electromagnetic radiation.

In the present invention a method is provided for determining optical properties of an object located in a turbid medium by: (1) generating a beam of amplitude modulated electromagnetic radiation which alternates between different colors at a predetermined modulation rate; (2) choosing the different colors so that each color interacts with the object differently, but so that the different colors also interact with the turbid medium in substantially the same manner; (3) applying the beam to the medium to generate diffuse photon density waves in the medium which interact with the object; (4) detecting output from the medium and storing a differential signal resulting from the alternating of colors at the predetermined modulation rate; and (5) deriving information about the optical properties of the object from the information contained in the differential signal.

According to the present invention there is also provided an apparatus for determining optical properties of an object located in a turbid medium including: (1) a source of amplitude modulated electromagnetic radiation which alternates between different colors at a predetermined modulation rate and such that the object interacts with the different colors differently but the medium interacts with the different colors substantially the same; (2) a device for applying the beam to the medium to generate diffuse photon density waves within the medium so that said diffuse photon density waves interact with the object; (3) a detector to receive the output from the medium and to store a differential signal resulting from alternation of the input by different colors; and (4) a processor to derive information about the optical properties of the object from the information contained in the differential signal.

BRIEF DESCRIPTION OF THE DRAWINGS

The invention may be more completely understood in consideration of the following detailed description of various embodiment of the invention in connection with the accompany drawings, in which.

DETAILED DESCRIPTION OF THE PREFERRED EMBODIMENTS

Figure 5:
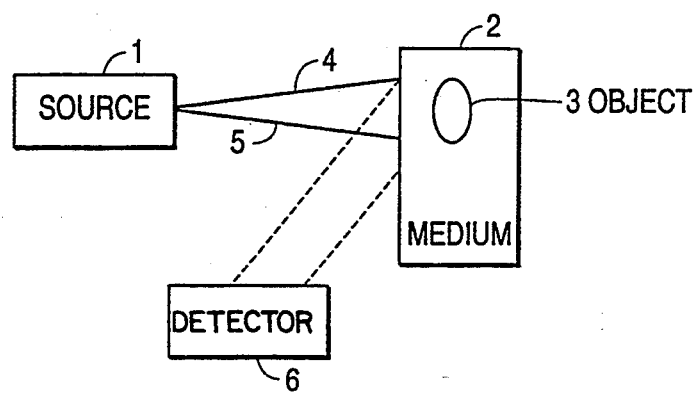
FIG. 5 shows a general diagram of the instant invention.

A detailed description of various embodiments of the invention will be described with reference to FIGS. 5 through 8. FIG. 5 shows a general diagram of an apparatus according to an embodiment of the instant invention. An electromagnetic radiation generating source 1 causes beams 4 and 5 to fall upon a turbid medium 2 containing an object 3.

While the principles behind the inventions may be applied to many different wavelengths of electromagnetic radiation, the invention is believed to be particularly useful with electromagnetic radiation sources falling within the range of 100 nm to 1 mm. The source of radiation is both amplitude modulated and frequency modulated. The term frequency modulation means that a carrier frequency of interest within the modulated wave is alternated between colors at a predetermined modulation rate. Hence, there is both a slight change in frequency (or wavelength) of the carrier wave to produce the different colors as well as a modulation rate (frequency) of change in color. The colors should be chosen so that the different colors react differently with the object 3, and at the same time the different colors must react in a similar manner with the medium 2.

While the preferred embodiment illustrates the use of two beams as shown, the inventions is not limited to such a device. The novel features of the invention can be readily applied to systems using one beam as well as two or more beams. The two beam configuration is shown to best illustrate the various aspects of the invention and is clearly useful in conjunction with the destructive and constructive interference techniques described above.

In the example shown, beams 4 and 5 are caused to follow different optical paths so that the amplitude modulation of one of the two beams is phase shifted from the other. The beams enter into the medium causing diffuse photon density waves. According to the phase shift, interference will occur between the waves. The output from the medium is detected by the detector 6. The detector 6 is such that it is capable of measuring a differential between the diffusive waves coming from the medium which vary at the modulation rate (i.e., the rate of changing color due to the frequency modulation) due to the different interaction with the object 3 by the different colors (i.e., the different colors interacting with the object 3 in a different manner).

Figure 1:
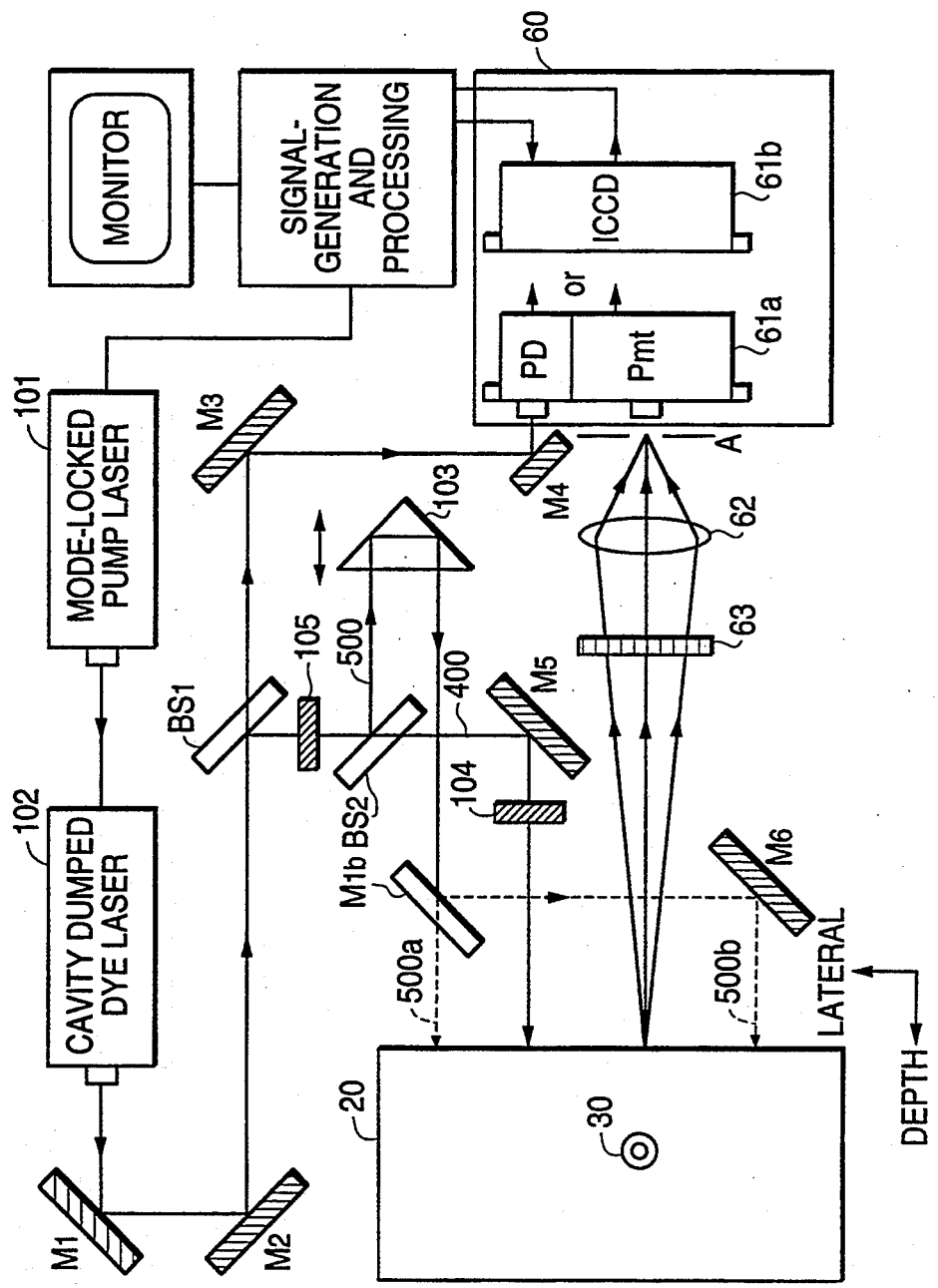
FIG. 1 shows an apparatus for imaging objects in turbid medium according to a prior art method.
Figure 2A:
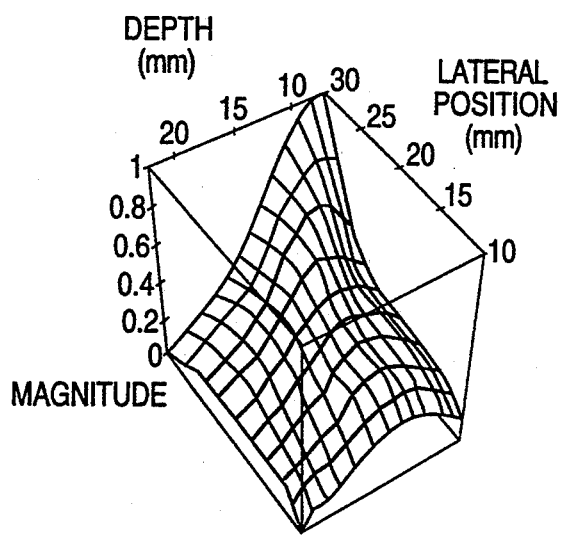
FIGS. 2a)–2d) show plots of magnitude and phase data induced by an absorbing body, located in both dimensions of the source/detector plane.
Figure 2B:
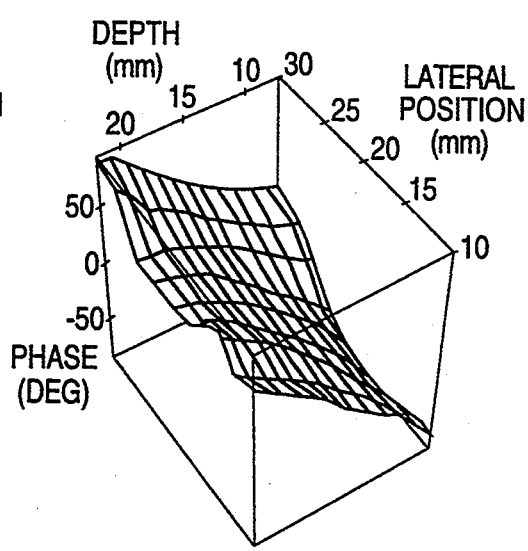
Figure 2C:
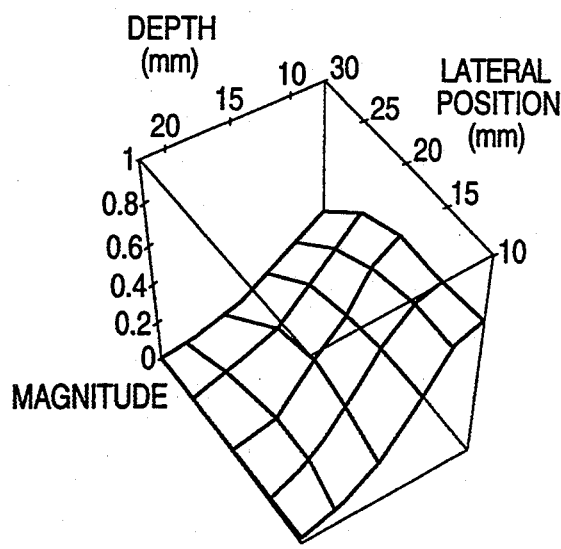
Figure 2D:
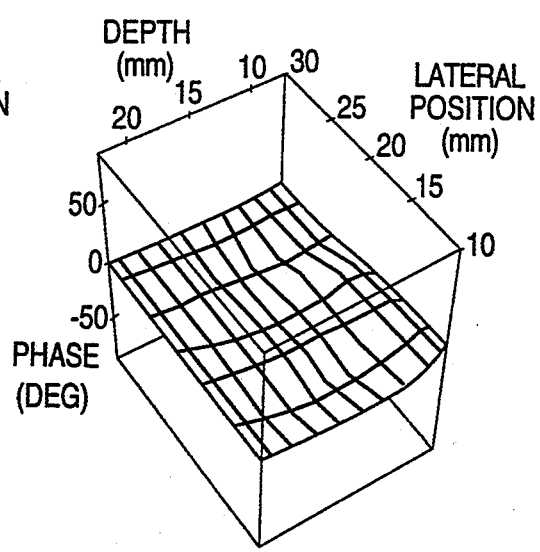
Figure 3A:
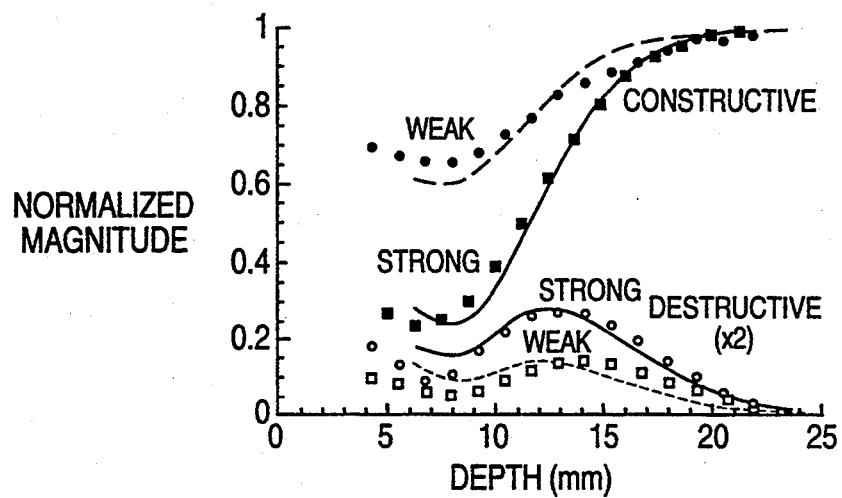
FIGS. 3a) and 3b) show plots of magnitude and phase data vs. depth location of the absorbing body for two different absorption coefficients (destructive and constructive interference)
Figure 3B:
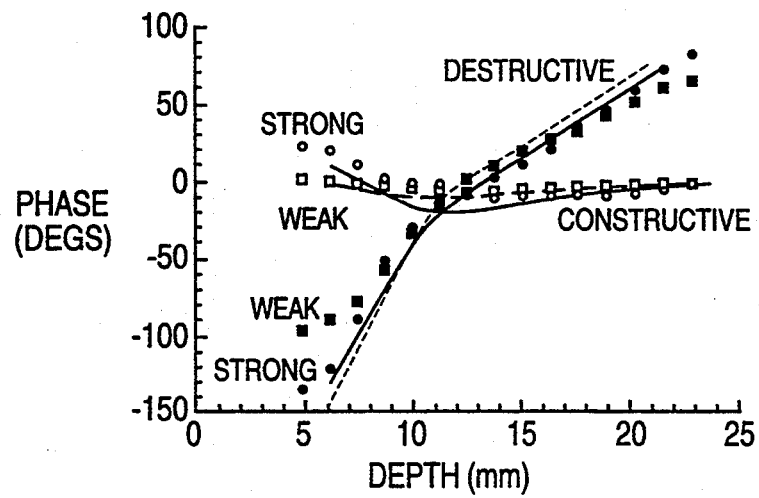
Figure 4E:
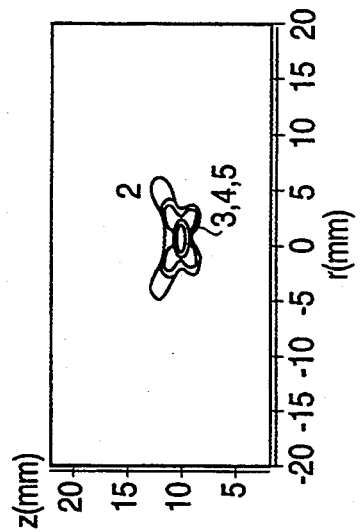
FIGS. 4a)–4e) show the magnitudes at different points in the medium (illumination pattern) calculated for constructive and destructive interference conditions.
Figure 4B:
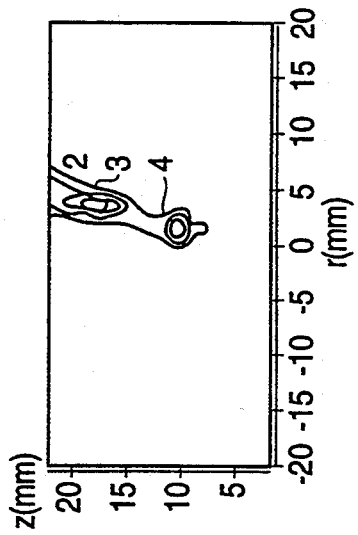
Figure 4D:
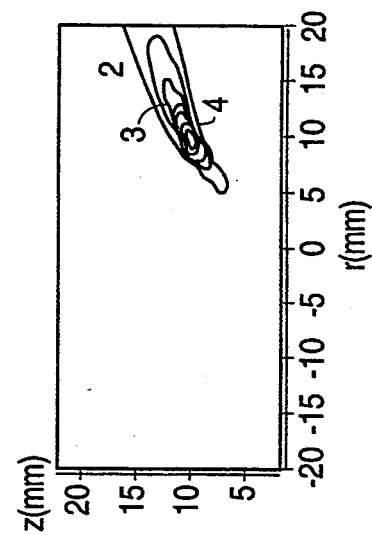
Figure 4A:
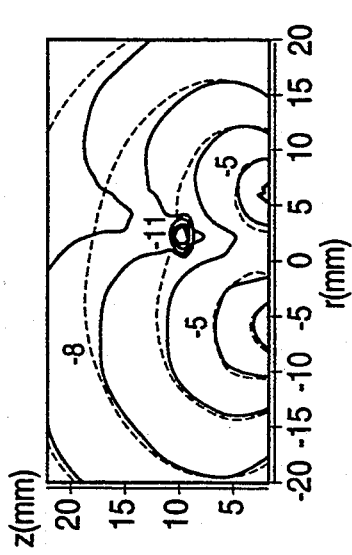
Figure 4C:
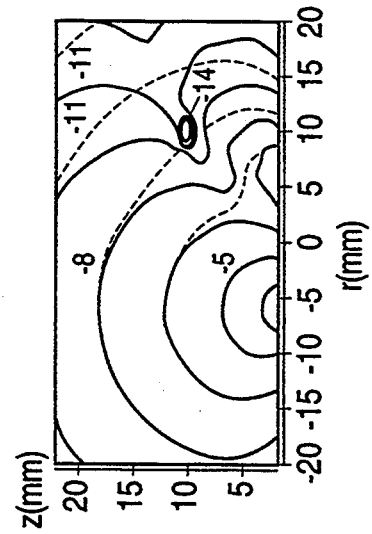
Figure 6:
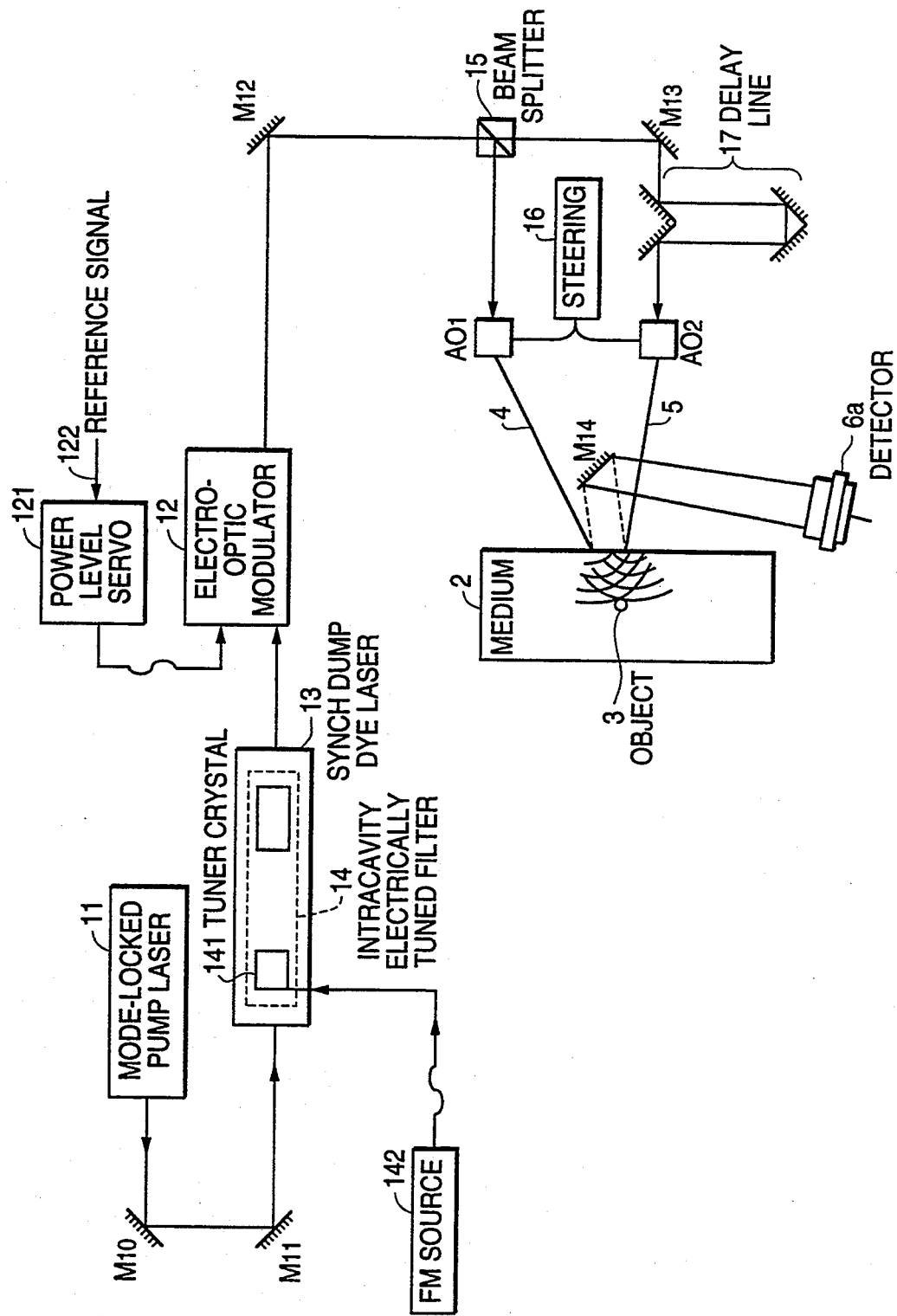
FIG. 6 illustrates a detailed implementation of an apparatus for accomplishing one embodiment of the invention.

FIG. 6 provides a more detailed depiction of an embodiment according to the invention. In the embodiment depicted in FIG. 6, various models of the individual elements shown can be used. Model numbers are provided as examples. When the elements used may be the same as those described in connection with the prior art model numbers are not provided. In FIG. 6 a mode-locked pump laser 11 is outputted via mirrors $M_{10}$ and $M_{11}$ to a synch pumped dye laser 13. An electro-optic modulator 12 (Electroscan LS-14K) receives the output from the synch pump dye laser 13. A power level servo 121 (any various type known in the art) is connected to the electro-optic modulation 12 to ensure that optical power between the different frequencies of the frequency modulation is maintained at equal levels. Alternatively, the power leveling mechanism can be inserted between the mode-locked pump laser 11 and the synch pump dye laser 13. The power level servo 121 is provided with a reference signal 122 from the laser output using beam splitters and mirrors (not shown). The synch pump dye laser 13 includes an intracavity electrically tuned filter 14. The intracavity electrically tuned filter 14 includes an electroscan tuner crystal (produced by Ithica research) and receives input from an FM source 142 (i.e., a source of varying voltage to modulate the frequency). The filter 14 preforms the frequency modulated (i.e., causes the source to alternate between two or more colors at a predetermined (modulation) rate). The source beam outputted from the synch pump dye laser is directed via mirror $M_{12}$ and through beam splitter 15 and delay line 17 to acousto-optic deflector modulators $AO_1$ and $AO_2$ (e.g., Isomet model LSHOxy) which are controlled by a steering mechanism 16. Steering mechanism 16 is a radio frequency source capable of amplitude and low frequency modulation to adjust the frequency and amplitude of the acoustic wave applied to acousto-optic deflectors $AO_1$ and $AO_2$. If a single beam is to be used, beam splitter 15 could be replaced with a mirror, thereby further eliminating the need for the mirror $M_{13}$, delay line 17 and acousto-optic deflector $AO_2$. Two or more beams are needed when interference between the photon density waves is to be exploited. The delay line 17 should be adjustable so that the optical path length of the second beam can be adjusted to create a phase shift between the density waves arising from the two beams incident upon the medium 2. This could be accomplished by using the prism and rail 103 configuration shown in FIG. 1. The acousto-optic deflectors steer the two separate beams 4 and 5 onto different parts of the medium. A diffuse photon density wave is generated in the medium where the beams interacts with the medium 2 and the density waves interact with the object 3. A mirror $M_{14}$ located on the input side of the medium picks up the optical image of the output returning from the medium and object and projects it onto the modulated detector 6a.

While the described apparatus operates in the reflectance-mode, it should be readily understood that the principles of the instant invention are also applicable to an apparatus operating in the transmittance-mode.

A signal from the modulated detector is sent to an electronic apparatus (described in FIG. 7) which interprets the data according to the differential between diffuse photon density wave output leaving the medium 2 at a frequency corresponding the an amplitude modulation frequency but slightly higher due to the frequency modulation. For example, the detector 6a is modulated at a particular frequency, 500 MHz, plus a small offset corresponding the modulation rate of changing colors (e.g., 50 Hz).

Figure 7:
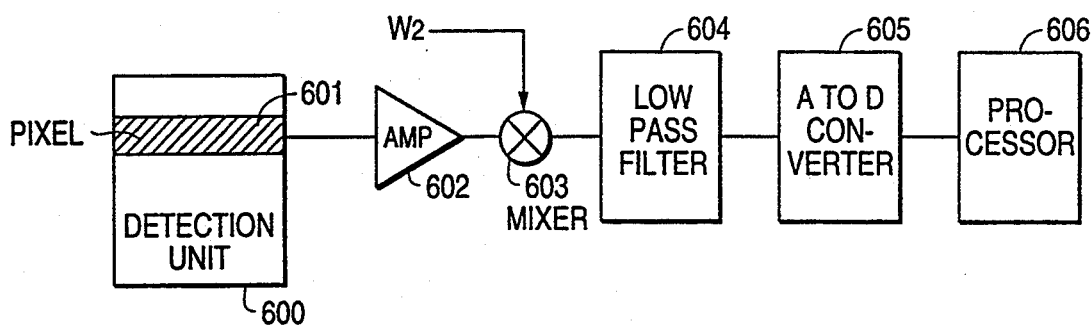
FIG. 7 shows a detailed depiction of a detector according to one embodiment of the invention.

The operation of the detector 6 according to an embodiment of the invention will be explained with reference to FIG. 7. In FIG. 7 a detection unit 600 includes a number of pixels. The output of each pixel is processed as shown. For example, pixel 601 is connected to amplifier 602. The output needs to be amplified due to the extreme damping caused by the turbid medium 2. The output from the amplifier 602 is provided to mixer 603 in order to down beat the output signal to a frequency which can be readily operated on by an analog to digital (A/D) converter 605 and processor 606. A low pass filter 604 may be placed between the mixer 603 and A/D convertor 605 to eliminate unwanted high frequencies. A frequency $\omega_2$ is supplied to the mixer and chosen to facilitate the desired down beating.

By way of example, consider the following illustration of the operation of the detector system. When the amplitude modulated signal is created it is also frequency modulated so that the carrier wave of the amplitude modulated wave alternates between different colors at a particular (predetermined) rate $\omega_3$. The rate of amplitude modulation is represented by $\omega_1$. Since the object 3 within the medium 2 interacts with the different colors differently, the output will be changing at the rate of the frequency modulation $\omega_3$. Hence, the output will have a component at a frequency equal to $(\omega_1 \pm \omega_3)$ representing the differential between the interaction of the colors. Strictly speaking, the information is also present at a low frequency corresponding to the value of $\omega_3$. However, if the system only looked at $\omega_3$, all information regarding the interference of the diffuse waves in the medium would be lost. Thus, the desired frequency for examination is $(\omega_1 \pm \omega_3)$. As representative examples, $\omega_1$ may equal 246 MHz and $\omega_3$ 10 Hz.

For convenience sake we just consider the case of $(\omega_1 + \omega_3)$. We note that if the object 3 interacts with the different colors in the same manner, the output value at a frequency equal to $(\omega_1 + \omega_3)$ would be zero. Since a frequency equal to $(\omega_1 + \omega_3)$ cannot be readily examined, the output is mixed (i.e., heterodyne down beat) with $\omega_2$ so that it is at a frequency which the A/D converter 605 can operate. $\omega_2$ is chosen at a value approximately equal to $\omega_1 + 100$ Hz $+ \omega_3$. The value examined after mixing will be at a frequency equal to $(\omega_1 \pm \omega_2 + \omega_3)$. In this case either the low pass filter 604 is used or the detector itself is so designed, to eliminated the higher frequency so that signal provided to the A/D converter is equal to $(\omega_1 - \omega_2 + \omega_3)$. The processor 606 will compute the fast Fourier transform (FFT) to examine the signal at the desired frequency (i.e., $(\omega_1 - \omega_2 + \omega_3)$). Thus, the information represented in the differential between the different interaction of different colors with the object 3 can be readily examined in real time (i.e., on line).

The term "differential signal" in the instant application refers a signal representing the difference between photon density waves of different colors. In effect, the differential measuring is performed by applying to the detector first and second patterns (corresponding to diffuse photon density waves resulting from first and second colors) in an alternating fashion at a particular rate $\omega_3$. The alternating signal having a frequency equal to the particular rate $\omega_3$ plus a frequency corresponding to the amplitude modulation $\omega_1$ (in order to maintain the information from the amplitude modulation) is detected by the detector. This signal represents how the output from the medium differs due to the change in color (i.e., different interaction by the object with the different colors).

By way of example, when slightly different colors are present in the frequency modulation, the components of the output pattern generated by the diffuse photon density waves caused by the scattering in the turbid medium will be substantially the same for both colors. Because the detection is based on a differential between the different colors, background components of the output (i.e., that which is not due to the object to be imaged) will be the same and can readily be removed. For example, if the object to be detected 3 absorbs light at one frequency generated by the frequency modulation but not at the second frequency generated by the frequency modulation, the signal received by the modulated detector 6 in effect compares the differential between the output information which changes at the rate of modulation In other words, the signal received by the modulated detector 6 is processed by heterodyne mixing to provide a differential between the two or more color interference patterns and to remove the common background interference. This information is detected when the appropriate frequency, $(\omega_1 - \omega_2 + \omega_3)$, is examined. It could be considered that one of the two diffuse wave patterns (i.e., diffuse wave pattern at one color) will have an pattern with a defect (or change) representing the object to be detected because the object to be detected absorbs the radiation at the particular color of that frequency. The second diffuse wave, however, will not have a defect (or change) in its pattern since the object to be detected 3 does not absorb the particular wavelength associated with the second color. As a result, the pattern will be changing at the rate of modulation, creating a component to the output detectable as described in connection with FIG.

7. When the pattern representing the unabsorbed pattern is effectively subtracted on line from the pattern which represents the absorbing pattern (i.e., the pattern with the hole created by the absorption of the object), the result will be a pattern specific to the characteristics of the absorbing object (i.e., the object for detection 3).

The differential pattern is actually examined by decomposing the output from the medium, which may be represented as a function f(t). The output function will be arbitrary in that it is dependent upon the random scattering and absorption of the medium. Since the pattern represented in f(t) is repeated according to the amplitude modulation it can be represented by a superposition (i.e., sum) of harmonic functions of different and complex amplitudes. One of these component harmonic functions, when the medium interacts differently for the different colors, will correspond to the a frequency equal to the frequency of amplitude modulation plus the frequency modulation rate (i.e., rate at which the colors are changed). This frequency corresponds to ($\omega_1+\omega_3$) as described in the above example in conjunction with the detector shown in FIG. 7. A component harmonic function at this frequency indicates that an object is interacting differently with the different colors, since the output function f(t) would not have a component at this frequency if both colors reacted identically with the object. Thus, the component at this frequency carries information about the object. From this type of information various optical characteristic of the object can be determined. One may view the object as a simple "source" of differential diffusive waves.

By use of an apparatus according to this invention, objects (or slight discolorations) may be imaged which have a slightly different color or density than the surrounding tissue. This is accomplished by setting one of the two or more colors of the frequency modulated beam at a wavelength which is absorbed by the object to be detected or the discoloration in the tissue, while choosing the other colors at wavelengths such that the object to be detected does not absorb the photons as strongly. This method allows for greater determination of the absorption characteristics and simplifies localization of the object within the tissue as compared to previous methods. Further, it may be possible using this technique to screen for discolorations, in breast tissue for example, which are not yet detectable by conventional methods.

Another advantage of this method is that real time differential amplification of signals is performed and information is obtained, greatly simplifying the task of comparing two difficult patterns. This is possible because the differential is performed in a domain separate from the setup of the system and, therefore, is performed in approximate real time.

Figure 8:
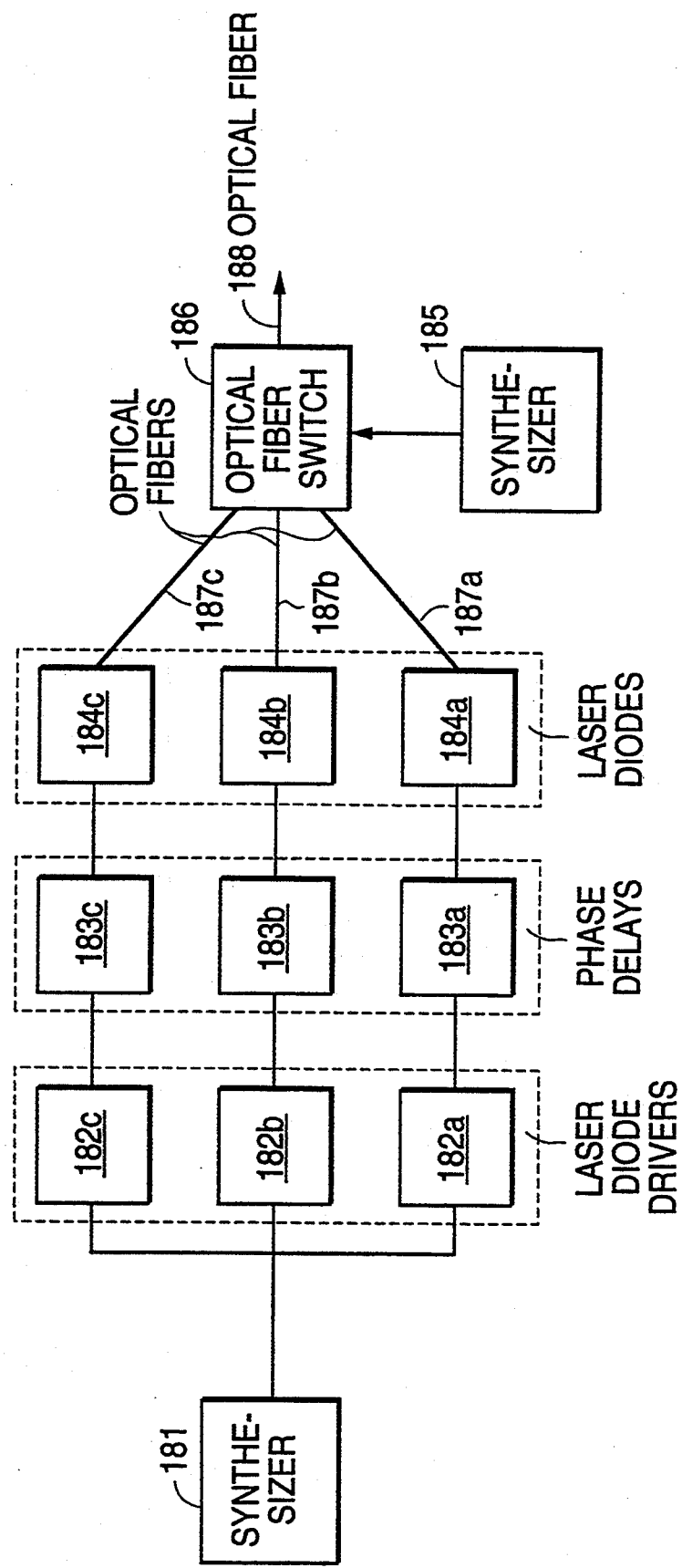
FIG. 8 illustrates a source of electromagnetic radiation according to an embodiment of the invention.

While the disclosed embodiments display a single laser with a intracavity electrically tuned filter creating the FM modulation, the invention is not limited to a single laser. For example, instead of using a single laser, two or more lasers each having slightly different frequencies may be used alternatingly at the rate $\omega_3$. A source of electromagnetic radiation according to such an embodiment is depicted in FIG. 8. According to this embodiment, three different laser diodes 184a, 184b and 184c are amplitude modulated by synthesizer 181. Each of the laser diodes corresponds to a different color. Between synthesizer 181 and the laser diodes 184a 184b and 184c are laser diode drivers 182a, 182b and 182c and phase delays 183a, 183b and 183c. The output from the laser diodes is fed via optical cables 187a, 187b and 187c to an optical fiber switch 186. The output via optical fiber 188 is controlled via the optical fiber switch 186 by synthesizer 185 to alternate between the different colors at a predetermined modulation rate $\omega_3$. The output via 188 may be directed against a medium and the resulting information may be collected and examined according to any of several devices constructed according to the above detection principles.

The acousto-optic deflectors and steering mechanism 16 depicted in FIG. 6, may also be used to scan the medium according to known techniques. The information obtained may then be applied over a scanned spatial region. For example, a graph may be created illustrating the presence and magnitude of an output component due to the changing colors and the different interaction when an object is present.

The above described embodiments are provided as an illustration of how the particular advantages of frequency modulation can be utilized to gain enhanced determinations of characteristics within a turbid medium. The invention is not limited to the particular devices disclosed, other variations and mechanisms for achieving the desired objectives will be readily understood by reference to the above described embodiments and falling within the scope of the appended claims.

What is claimed is:

1. A method for determining an optical property of an object located in a turbid medium comprising the steps of:
   generating a beam of amplitude modulated electromagnetic radiation which alternates between different colors at a predetermined modulation rate;
   choosing said different colors such that said different colors interact with said object differently while interaction between said different colors and said turbid medium is substantially the same;
   applying said beam to said medium to generate diffuse photon density waves within said medium such that said diffuse photon density waves interact with said object;
   detecting output from said medium and storing a differential signal resulting from said modulation at said predetermined modulation rate; and
   deriving information about said optical property of said object from said differential signal.

2. A method as recited in claim 1 wherein said choosing step comprises choosing said different colors such that one of said different colors is absorbed by said object and another of said different colors is not absorbed by said object.

3. A method as recited in claim 1 further comprising the step of leveling optical power of said beam so that optical power associated with each of said different colors is substantially equal.

4. A method as recited in claim 1 further comprising the steps of:
   splitting said beam into at least two beams; and
   applying multiple beams to said medium.

5. A method as recited in claim 4 further comprising the step of generating a phase difference between at least two of said multiple beams so as to produce one of constructive and destructive interference of said diffuse photon density waves.

6. A method as recited in claim 1 further comprising the step of scanning said beam across a portion of said medium.

7. A method as recited in claim 1 further comprising the step of spatially localizing said object utilizing said information about said optical property.

8. A method as recited in claim 1 wherein said generating step further comprises the step of generating said electromagnetic radiation such that the wavelength of said electromagnetic radiation is in the range between 100 nm to 1 mm.

9. A method as recited in claim 1 wherein said generating step further comprises the steps of:
generating individual pulses from at least two different lasers, said different lasers corresponding to said different colors;
optically combining output of said individual lasers to form a single beam path; and
timing said individual pulses in accordance with said predetermined modulation rate to generate said beam alternating between said different colors.

10. An apparatus for determining an optical property of an object located in a turbid medium comprising:
a source of amplitude modulated electromagnetic radiation which alternates between different colors at a predetermined modulation rate, said different colors selected such that said object interacts with said different colors differently and said medium interacts with said different colors substantially the same;
means for applying said beam to said medium to generate diffuse photon density waves within said medium such that said diffuse photon density waves interact with said object;
means for receiving the output from said medium and storing a differential signal resulting from said modulation at said predetermined modulation rate; and
means for deriving information about said optical property of said object from said differential signal.

11. A apparatus as recited in claim 10, wherein one of said different colors is absorbed by said object and another of said different colors is not absorbed by said object.

12. A apparatus as recited in claim 10, further comprising means for leveling optical power of said beam so that optical power associated with each of said different colors is substantially equal.

13. A apparatus as recited in claim 10, further comprising:
means for splitting said beam into at least two beams; and
means for directing multiple beams to said medium.

14. A apparatus as recited in claim 13, further comprising the step of generating a phase difference between at least two of said multiple beams so as to produce one of constructive and destructive interference of said diffuse photon density waves.

15. A apparatus as recited in claim 10, further comprising means for scanning said beam across a portion of said medium.

16. A apparatus as recited in claim 10, further comprising means for spatially localizing said object utilizing said information about said optical property.

17. A apparatus as recited in claim 10, wherein said electromagnetic radiation comprises Wavelengths in the range between 100 nm to 1 mm.

18. A apparatus as recited in claim 10, wherein said source comprises:
at least two different lasers, said different lasers corresponding to said different colors;
means for optically combining output of said individual lasers to form a single beam path; and
means for alternating said individual pulses in accordance with said predetermined modulation rate to generate said beam alternating between said different colors.

19. A method for determining an optical property of an object located in a-turbid medium comprising the steps of:
generating a beam of amplitude modulated electromagnetic radiation which is frequency modulated to alternate between different colors at a predetermined modulation frequency;
choosing said different colors such that said different colors interact with said object differently while interaction between said different colors and said turbid medium is substantially the same;
applying said beam to said medium to generate diffuse photon density waves within said medium such that said diffuse photon density waves interact with said object;
detecting output from said medium and generating a signal corresponding to said output;
processing said signal such that phase and amplitude information arising from modulations in photon density from both said amplitude modulation frequency and said frequency modulation frequency is retained; and
deriving information about a location of said object and said optical property of said object by analyzing a spatial pattern and color variation in said phase and amplitude information.

20. A method as recited in claim 19, wherein said processing step further comprises the steps of:
heterodyne mixing said signal from a photodetector with a predetermined frequency to produce a mixed signal;
filtering said mixed signal to produce a filtered signal;
convert said filtered signal to a digital signal to facilitate processing; and
isolating components of said signal at frequencies corresponding to combinations of said amplitude modulated frequency, said frequency modulation frequency and said predetermined frequency.

21. An apparatus for determining a property of an object located in a medium, comprising:
a source of amplitude modulated electromagnetic radiation which is frequency modulated between different frequencies at a predetermined modulation rate, said different frequencies being selected such that said object interacts with said different frequencies differently and said medium interacts with said different frequencies substantially the same, said source of electromagnetic radiation being incident upon said medium;
a detector located to detect at least a portion of said electromagnetic radiation after said portion has interacted with said object and said medium, said detector producing an output signal representative of said detected electromagnetic radiation; and
a processor coupled to receive said output signal, said processor determining said property of said object from said output signal.

* * * * *